United States Patent [19]

Hsieh

[11] Patent Number: 5,249,123
[45] Date of Patent: Sep. 28, 1993

[54] COMPENSATION OF COMPUTED TOMOGRAPHY DATA FOR DETECTOR AFTERGLOW

[75] Inventor: Jiang Hsieh, Waukesha, Wis.

[73] Assignee: General Electric Company, Milwaukee, Wis.

[21] Appl. No.: 797,620

[22] Filed: Nov. 25, 1991

[51] Int. Cl.⁵ .................... G06F 15/00; G01N 23/00
[52] U.S. Cl. .................... 364/413.19; 364/413.22; 364/413.13; 378/19
[58] Field of Search .......... 364/413.19, 413.13, 364/507, 413.22; 378/19; 358/101; 73/625

[56] References Cited

U.S. PATENT DOCUMENTS

| | | | |
|---|---|---|---|
| 4,112,303 | 9/1978 | Brandt | 250/445 T |
| 4,494,141 | 1/1985 | Alterkruse | 358/111 |
| 4,583,240 | 4/1986 | Gatten et al. | 378/19 |
| 4,590,558 | 5/1986 | Glover et al. | 364/414 |
| 5,008,822 | 4/1991 | Brunnett et al. | 364/413.21 |

Primary Examiner—Roy N. Envall, Jr.
Assistant Examiner—Khai Tran
Attorney, Agent, or Firm—Quarles & Brady

[57] ABSTRACT

A medical imaging system includes a source of X-rays and a radiation detector that produces an output signal in response to radiation from the source. The detector has an exponential impulse response that is characterized by a plurality of components with different time constants. The output signal from the detector is sampled periodically to acquire a set of radiation attenuation values. A recursive filter applies a filter function to the set of attenuation values that removes effects due to the non-ideal impulse response of the detector. The filter function includes a term for each of the time constant components. An image is reconstructed from the filtered data.

9 Claims, 4 Drawing Sheets

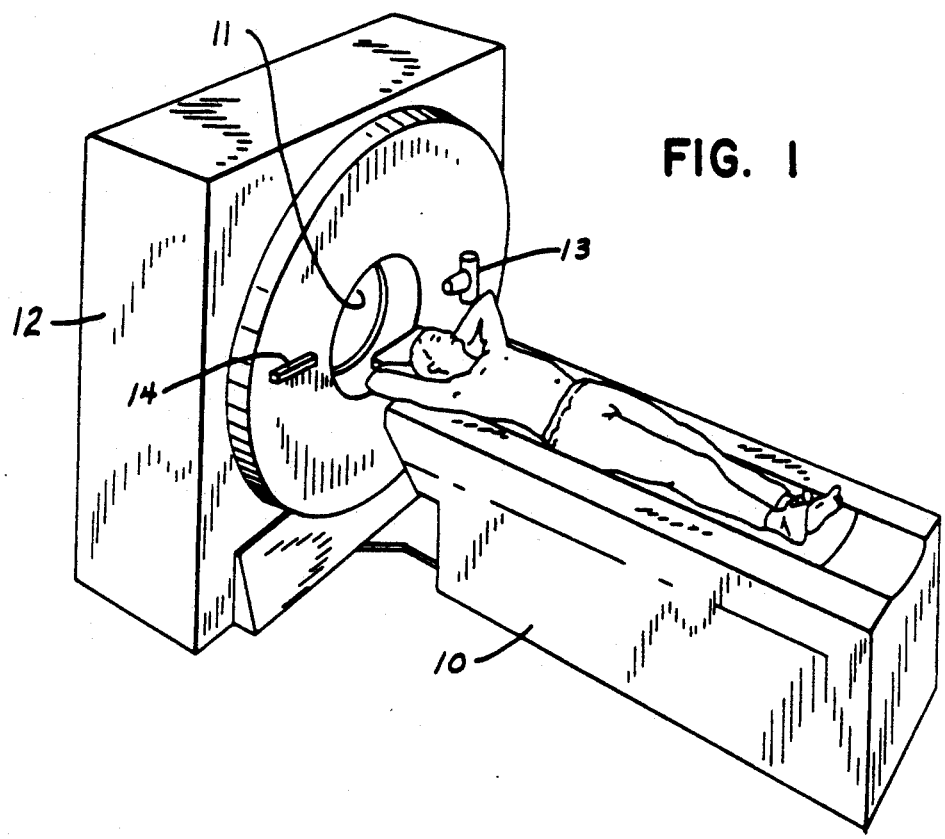
FIG. 1
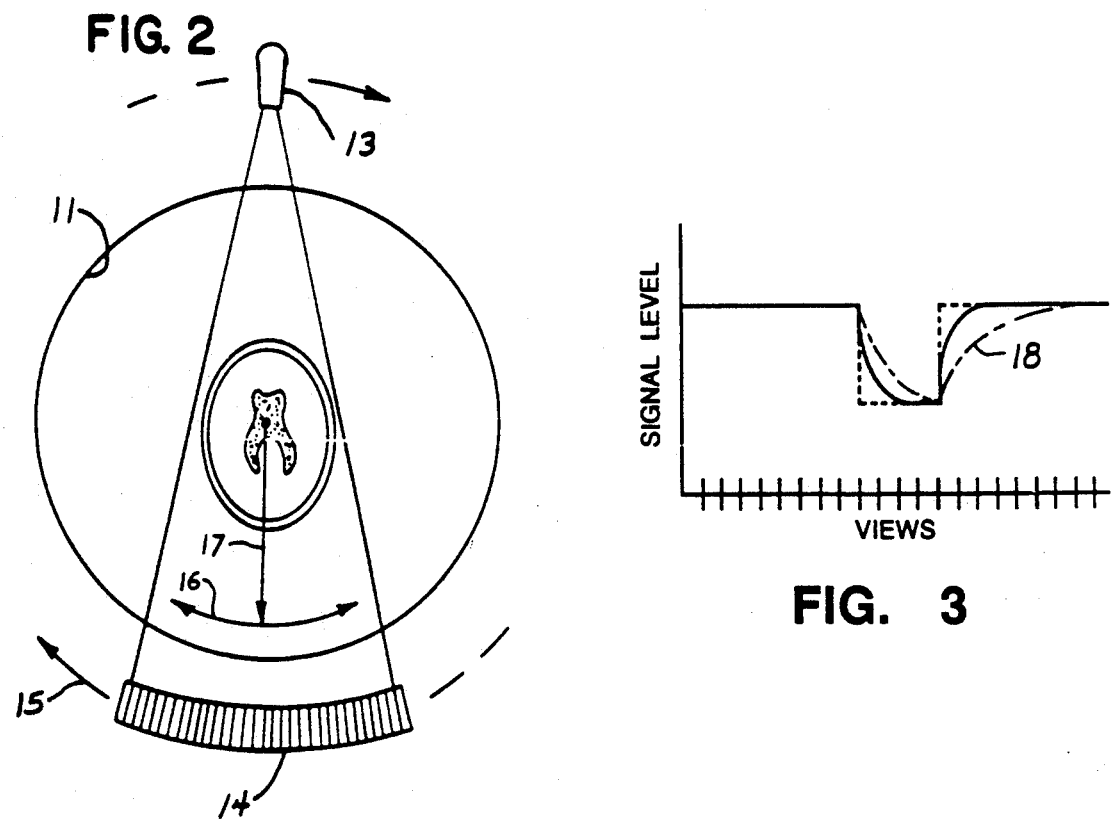
FIG. 2
FIG. 3

COMPENSATION OF COMPUTED TOMOGRAPHY DATA FOR DETECTOR AFTERGLOW

BACKGROUND OF THE INVENTION

The present invention relates generally to computed tomography (CT) scanners which produce images from X-ray attenuation measurements, and particularly to techniques for removing artifacts from such images.

As shown in FIG. 1, a CT scanner for producing images of the human anatomy includes a patient table 10 which can be positioned within the aperture 11 of a gantry 12. A source of highly collimated X-rays 13 is mounted within the gantry 12 to one side of its aperture 11, and one or more detectors 14 is mounted to the other side of the aperture. The X-ray source 13 and detectors 14 revolve about aperture 11 during a scan of the patient to obtain X-ray attenuation measurements from many different angles.

A complete scan of the patient is comprised of a set of X-ray attenuation measurements which are made at different angular orientations of the X-ray source 13 and detector 14. The gantry may stop or continue to move as the measurements are being made. Each such set of measurements is referred to in the art as a "view" and the results of each such set of measurements is a transmission profile. As shown in FIG. 2, the X-ray source 13 produces a fan-shaped beam which passes through the patient and impinges on an array of detectors 14. Each detector 14 in this array produces a separate attenuation signal and the signals from all the detectors 14 are separately acquired to produce the transmission profile for the indicated angular orientation. The X-ray source 13 and detector array 14 continue to revolve in direction 15 to another angular orientation where the next transmission profile is acquired.

As the data are being acquired for each transmission profile, the signals are sampled, filtered and stored in a computer memory. The signals from the detectors are over sampled to provide twice the number of transmission profiles as are required to reconstruct an image, for example. The attenuation measurement samples then are digitally low-pass filtered and the output of the filtering is sampled at a rate that produces the required number of transmission profiles from which to reconstruct an image. These steps are performed in real time as the data is being acquired.

The resultant transmission profiles then are used to reconstruct an image which reveals the anatomical structures in a slice taken through the patient. The prevailing method for reconstructing image is referred to in the art as the filtered backprojection technique. The attenuation measurements are converted to integers called "CT numbers" or "Hounsfield units", which are used to control the brightness of a corresponding pixel on a CRT display.

Each X-ray detector 14 comprises a scintillator and a solid state photodiode. X-rays striking the scintillator produce light photons which are absorbed by the photodiode creating an electric current. The light is not emitted by the scintillators instantaneously, rather the emission follows a multi-exponential curve. Similarly the light emission does not terminate immediately when the X-ray beam is cut off, but follows a multi-exponential curve. The time dependence of the emitted light intensity can be modelled accurately as a sum of several exponential terms with different decay constants.

Because the detector array is rotating rapidly about the patient, the exponential response blurs together detector readings for successive views producing an image artifact referred to as "afterglow". The afterglow degrades the azimuthal component of the image resolution which produces shading and arc shaped artifacts in the reconstructed image. The azimuthal direction 16 of the image area is perpendicular to a line 17 from the center of the imaging aperture 11.

FIG. 3 plots attenuation values from a given detector for a series of views and graphically depicts the blurring. The solid line represents the output of a single detector 14 during several views for a square object being imaged. Ideally the detector data should have a pulse-like shape as represented by the dashed lines. However, the effect of the afterglow rounds the edges of the waveform and extends the object signal into several adjacent views. When the views are used to reconstruct an image, the object will appear enlarged and will not have sharp, distinct edges. In addition, if the response of individual detectors vary (e.g. an adjacent detector may have a response shown by line 18), an inconsistence will be created in the projection which leads to arc artifacts.

An obvious solution to the resolution degradation and artifacts is to slow the rotational speed of the X-ray source and detectors and provide a delay between views that is long enough for the afterglow to decay to a negligible level. This prolongs image acquisition making the process more susecptible to patient motion artifacts. Heretofore, an minor amount of degradation has been tolerated, but as rotational scan periods become shorter, approaching one second for example, the image degradation reaches unsatisfactory levels.

SUMMARY OF THE INVENTION

A computed tomography imaging system includes a source of radiation and a detector array which senses radiation from said source and produces an output signal representing the sensed radiation. Every detector has an exponentially decaying impulse response that can be modelled accurately as a sum of a plurality of N components with different time constants. The most prompt time constant component is referred to as "primary speed" and is the time in which the detector output falls to 1/e of its initial value after being stimulated by an impulse of X-rays. The remaining time constant components are referred to collectively as the "afterglow".

A means is provided which samples the output signals from the detectors to produce a set of radiation attenuation values at periodic intervals $\Delta t$. There are K attenuation values acquired from each detector during a scan.

A recursive filter applies a filter function to each attenuation value $y(k\Delta t)$ in the sets to remove the effects of the exponential decay and produce a filtered value $x_k$, where k designates the view during which the sample was acquired. In the preferred embodiment the filter function is defined by the expression:

$$x_k = \frac{y(k\Delta t) - \sum_{n=1}^{N}(\beta_n e^{-\Delta t/\tau_n})S_{nk}}{\sum_{n=1}^{N}\beta_n}$$

where $\beta_n = \alpha_n(1-e^{-\Delta t/\tau_n})$ in which $\alpha_n$ represents the relative strength of the response component with time constant $\tau_n$, and $S_{nk} = x_{k-1} + e^{-\Delta t/\tau_n} S_{n(k-1)}$. An image is reconstructed from the set of filtered values by conventional techniques, such as by a filtered backprojection process.

An object of the present invention is to provide to a technique which alters the X-ray attenuation measurements from each detector to remove the effects produced by a non-ideal radiation response of the detector.

Another object is to provide a technique which removes artifacts due to both primary speed and afterglow effects.

A further object of the present invention is to provide a filtering operation that compensates for the different components of the multi-exponential response of the radiation detector.

Yet another object of the present invention is to provide a process for characterizing the response of a given detector.

BRIEF DESCRIPTION OF THE DRAWINGS

FIG. 1 is a perspective view of a CT imaging system in which the present invention may be employed;

FIG. 2 is a schematic representation of a scanning technique employed in the CT imaging system;

FIG. 3 is a graph illustrating the detector readings for an ideal detector and an actual detector which has resolution degradation due to afterglow;

DESCRIPTION OF THE PRESENT INVENTION

Figure 4:
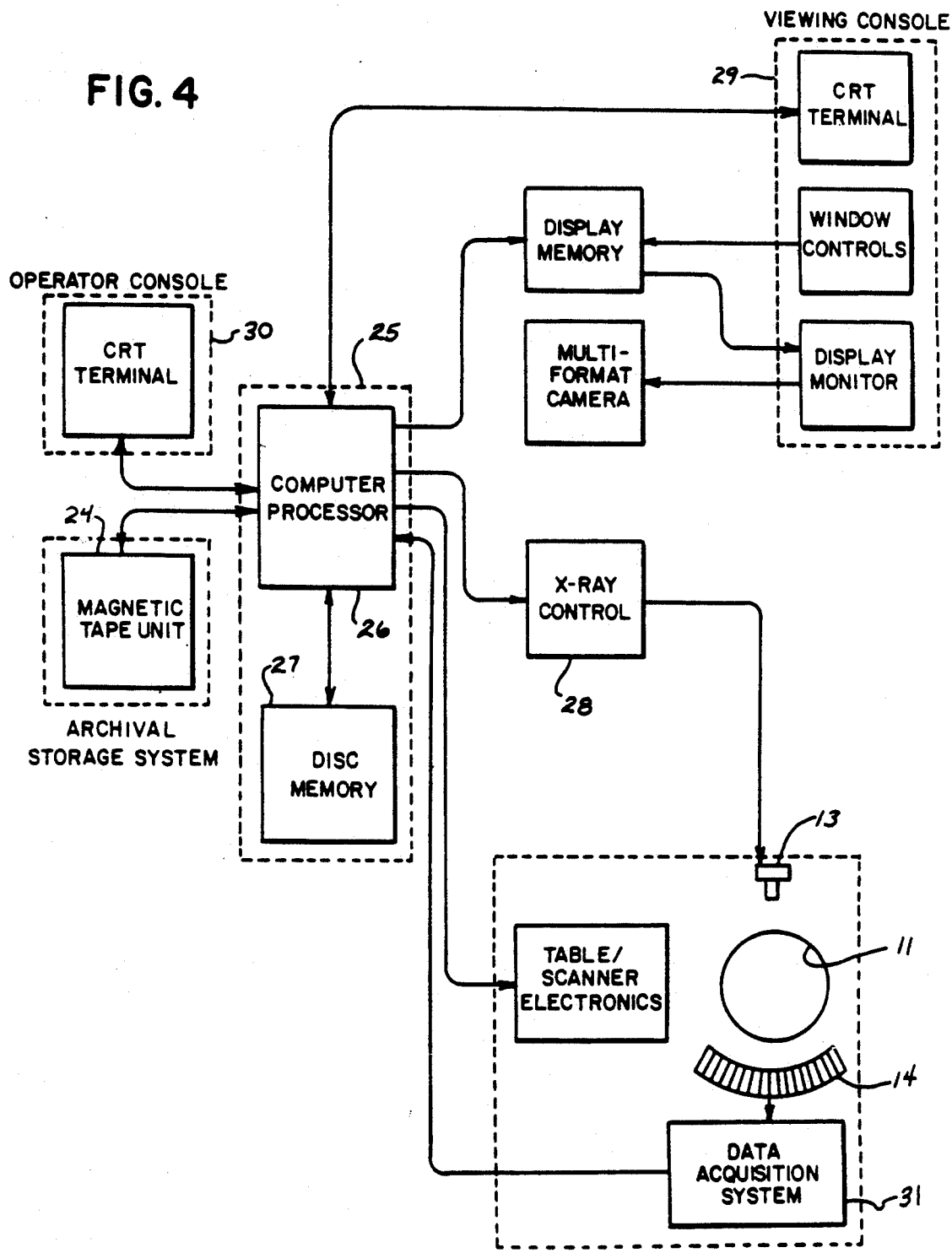
FIG. 4 is a block diagram of the signal processing circuitry in the CT imaging system.
Figure 5:
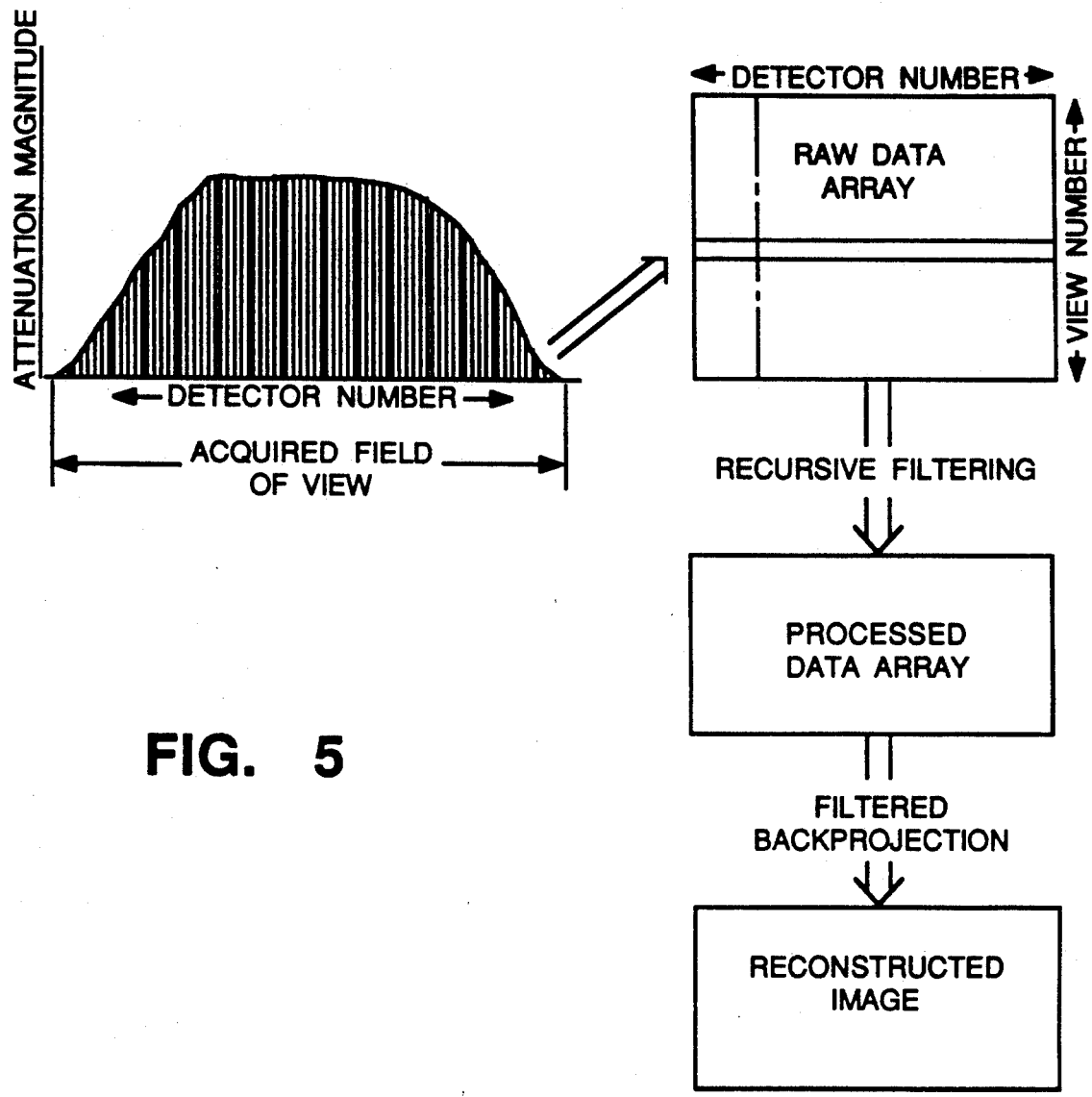
FIG. 5 is a graphical representation of data which is acquired and processed by the CT imaging system.
Figure 6:
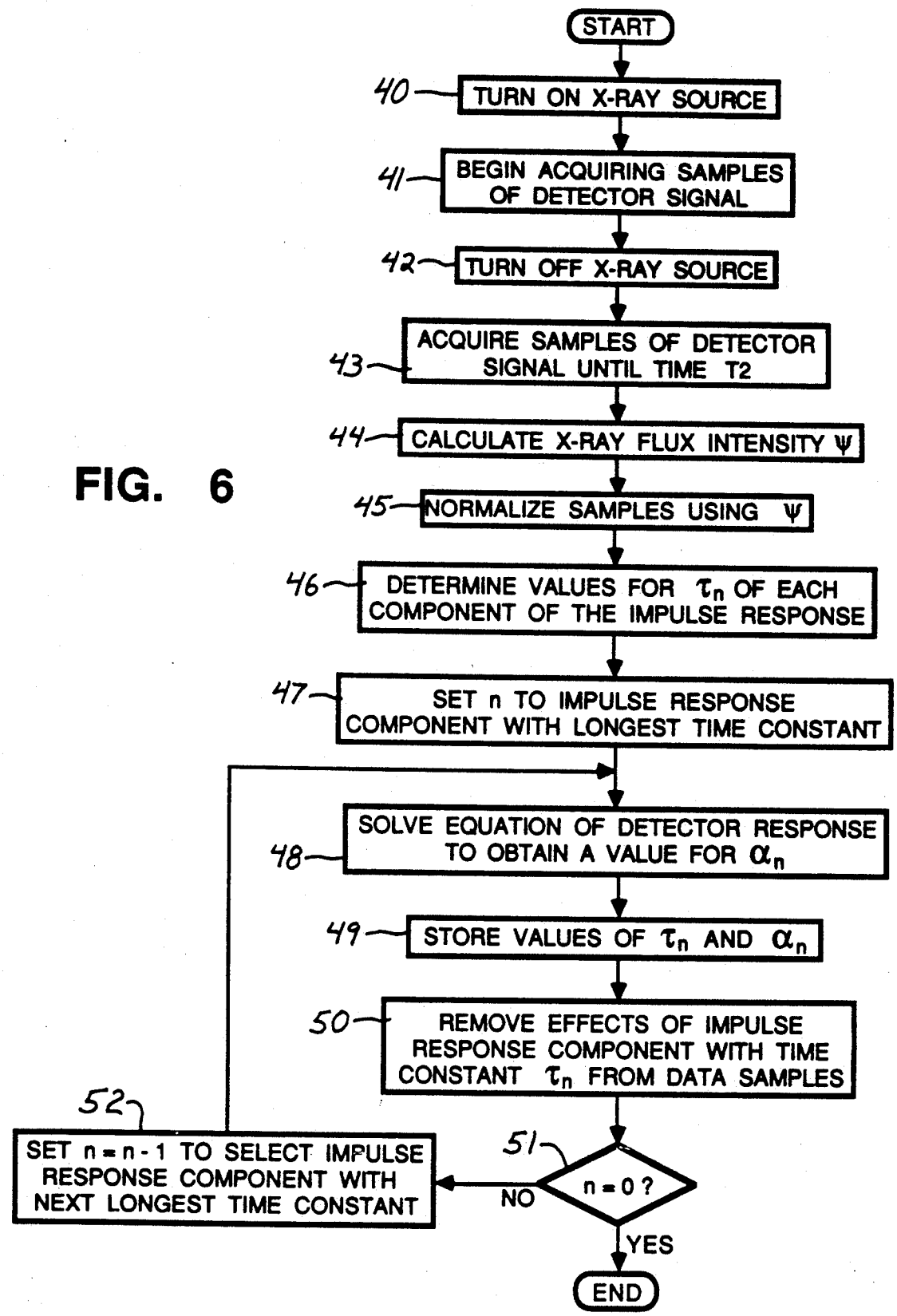
FIG. 6 is a flowchart of a process by which a detector is characterized.

With reference to FIGS. 1, 2 and 4, the operation of the CT imaging system is controlled by a programmable data processing system 25 which includes a computer processor 26 and a disc memory 27. The disc memory 27 stores the programs that the computer processor 26 uses in patient scanning and in image reconstruction and display. It also stores, on a short-term basis, the acquired data and the reconstructed image data. The computer processor 26 includes a general purpose minicomputer with input and output ports suitable for connection to the other system components as shown and an array processor such as that disclosed in U.S. Pat. No. 4,494,141. The description of the array processor in that patent is incorporated herein by reference.

An output port on the computer processor 26 connects to an X-ray control circuit 28, which in turn controls excitation of the X-ray source 13. The high voltage on the X-ray source 13 is controlled and its cathode current is regulated to provide the correct dosage. The high voltage and cathode current are selected by a user who enters the desired values through an operator console 30 and the computer processor 26 directs the production of the X-rays in accordance with its scan program.

The X-rays disperse in a fan-shape described previously and are received by the array of detectors 14 mounted on the opposite side of the gantry aperture 11. Each individual detector examines a single ray originating from the X-ray source 13 and traversing a straight line path through a patient located in the aperture 11. The detector array also includes a group of reference detectors at each of its ends that receive unattenuated X-rays from the source 13. The currents formed in each detector 14 are collected as an analog electrical signal and converted into a digital number by analog to digital converters in a data acquisition system 31. The signals are digitized sequentially starting at one end of the detector array and finishing at the other end. The digitized signals are input to the computer processor 26. The digitized measurements from all the detectors is a complete view.

U.S. Pat. Nos. 4,112,303 and 4,115,965 disclose the details of the gantry construction, U.S. Pat. No. 4,707,607 describes the detector array 14, and the data acquisition system is disclosed in U.S. Pat. No. 4,583,240. The descriptions of the system components in these patents are incorporated herein by reference.

The digitized attenuation measurements from the data acquisition system 31 are preprocessed in a well known manner to compensate for "dark currents", uneven detector sensitivities and gains, and variation of the X-ray beam intensity throughout the scan. This is followed by beam hardening corrections and conversion of the data to logarithmic form so that each measured value represents a line integral of the X-ray beam attenuation. This preprocessing is performed in real-time while the scan is occurring and the attenuation values 32 in each view are stored as one row of a two-dimensional raw data array in the disc memory 27. Each of these rows of attenuation data provides a transmission profile of the object to be imaged when viewed from a single angle. Each column of data in the array represents the data acquired from a given detector during the scan. The present invention separately processes each column of data to remove the artifacts due to the primary speed and afterglow.

At the completion of the scan, the array of raw data contains, in each of its rows, a transmission profile from one view. Therefore, one dimension of this array is determined by the number of views, or attenuation values, which are acquired during the scan and the other dimension is determined by the number of detectors sampled during each view. For example, signals from up to 852 detectors may be sampled approximately 1,000 times during a scan to produce an equivalent number of views.

The raw attenuation data stored in array has been corrupted by the primary speed and afterglow effects due to the response time lag of each detector. If the raw data are used to reconstruct an image, features of the image will be blurred as described previously. However, the present system provides a mechanism which compensates for resolution degradation, shading and arc artifacts due to these effects. In order to define the compensation, or filtering mechanism, the response the type of detector used in the array has to be characterized.

The impulse response of each detector (i) in the array can be modelled by the equation:

$$h(t) = \sum_{n=1}^{N} \frac{\alpha_n}{\tau_n} e^{-t/\tau_n} \qquad (1)$$

where n designates one of N components of the exponential response which has a relative strength $\alpha_n$ and a time constant $\tau_n$. The response of one type of detector has been characterized accurately by four (N=4) such time constant components.

In order to determine a correction mechanism for the image artifacts, one must understand the afterglow effect. The detector response y(t) to input signal x(t) can be expressed as the convolution of the detector impulse response h(t) and the input signal x(t):

$$y(t) = h(t) * x(t) \qquad (2)$$

$$y(t) = \int_{-\infty}^{t} x(t') \sum_{n=1}^{N} \frac{\alpha_n}{\tau_n} e^{-(t-t')/\tau_n} dt'$$

Equation (2) can be simplified because the input signal x(t) is a causal function, allowing the summation and integration to be interchanged in equation (2). Furthermore the integration region [0,t] can be divided into k intervals corresponding to the period between views with each interval being denoted by $\Delta t$ ($k\Delta t = t$). When these factors are considered, the actual attenuation value $x_k$ for the kth view can be expressed for relatively small values of $\Delta t$ by the equation:

$$x_k = \frac{y(k\Delta t) - \sum_{n=1}^{N} \alpha_n (1 - e^{-\Delta t/\tau_n}) \sum_{j=1}^{k-1} x_j e^{-(k-j)\Delta t/\tau_n}}{\sum_{n=1}^{N} \alpha_n (1 - e^{-\Delta t/\tau_n})} \qquad (3)$$

where $y(k\Delta t)$ is the raw attenuation value from the detector acquired during the kth view. Although this equation expresses the relationship between the sample of the detector signal and the actual radiation level that produced that sample, it can not be implemented easily as the calculation for a given value requires values for the detector samples from all the previous views in current scan.

To overcome that difficulty equation (3) can be rewritten into the form:

$$x_k = \frac{y(k\Delta t) - \sum_{n=1}^{N} \beta_n e^{-\Delta t/\tau_n} [x_{k-1} + e^{-\Delta t/\tau_n} [x_{k-2} + \ldots + e^{-\Delta t/\tau_n} (x_2 + e^{-\Delta t/\tau_n} x_1)\ldots]]}{\sum_{n=1}^{N} \beta_n}$$

where $\beta_n = \alpha_n (1 - e^{-\Delta t/\tau_n})$. If the contents enclosed by the outermost brackets in the immediately preceding equation are denoted as $S_{nk}$, the following relationship exists:

$$x_k = \frac{y(k\Delta t) - \sum_{n=1}^{N} (\beta_n e^{-\Delta t/\tau_n}) S_{nk}}{\sum_{n=1}^{N} \beta_n} \qquad (5)$$

where the denominator and the bracketed portion of the numerator are constants. The term $S_{nk}$ for the present attenuation value is a function of that term $S_{n(k-1)}$ for the attenuation value from the previous view, as given by $S_{nk} = x_{k-1} + e^{-\Delta t/\tau_n} S_{n(k-1)}$, in which $x_{k-1}$ is the actual attenuation value derived from the detector signal sample from the previous view. The value of $S_{nk}$ for the first sample is zero. Thus to derive the actual attenuation value from a given detector signal sample, only that sample and data from the processing of the immediately preceding sample need to be known. As a result, equation (5) can be implemented by the array processor as a recursive filter.

In order to apply the filter function in equation (5) to real image data, the response for each detector in the array 14 must be characterized by deriving values for $\alpha_n$ and $\tau_n$ for the time constant components of each detector. This is accomplished in the factory by operating the CT system without an object present in the imaging aperture 11. The X-ray source 13 turned on at time $t_0$ for a period of time that is sufficiently long so that the detector response can reach its full magnitude, e.g. approximately half of the normal scan time at step 40. The X-ray beam then is turned off at time $t_1$ at step 42.

The output signal from each detector in array 14 is sampled individually while the X-ray beam is active and for one second thereafter, for example at steps 41 and 43. The samples of the detector signals are stored in an array similar to the one used for the attenuation values during actual imaging.

The detector response during the characterization process is defined by the expressions:

$$y(t) = \psi \text{ for } t_0 < t < t_1, \text{ and} \qquad (6)$$

$$y(t) = \psi \sum_{n=1}^{N} \alpha_n e^{(t-t_1)/\tau_n} \text{ for } t \geq t_1.$$

The samples of the detector output signal that were acquired while the X-ray beam is on ($t_0 < t < t_1$) are averaged and the result is used to derive a value for the X-ray flux intensity $\psi$ according to equation (6) at step 44. The samples acquired after the termination of the X-ray beam is divided by the value of $\psi$ to normalize the data at step 45 and the logarithm of the normalized data then is taken.

Then values for $\alpha_n$ and $\tau_n$ of each time constant component of the exponential response are determined next. The impulse response for one type of CT detector is characterized by four time constants $\tau_n$ of 1, 6, 40 and about 300 milliseconds, although the exact time constants may vary for other detectors. These time constants were determined graphically by plotting the detector signal samples representing the decay for a number of detectors of the same type and averaging the resultant time constants. The set of time constants at step 46 then are used in determining a value of the relative strength $\alpha_n$ of the corresponding impulse response component of other detectors. Although using a common set of time constants appears to be satisfactory in determining values for $\alpha_n$, a set of time constants can be derived individually for each detector being characterized.

The values of $\alpha_n$ for a given detector are found in descending order starting with the response component having the longest time constant (e.g. n=4) at step 47. A detector signal sample is selected that was acquired at time T (e.g. 300 milliseconds) after the X-ray beam extinguished at which time the effects of all except the longest time constant component are negligible. Using the logarithmic values of the detector samples equation (6) can be simplified to $\log[y(T)] = \log \alpha_n - (T/\tau_n)$. The simplified equation is solved for $\alpha_4$ of the fourth (n=4) time constant component at steps 48 and 49.

Based on the estimated values for $\alpha_4$ and $\tau_4$, the contribution of the longest time constant component to the measured decaying signal data can be calculated and removed from that data at step 50. The process is repeated for the next longest time constant component of the detector response, and so on for each of the remaining components see steps 51 and 52. This characterization process is performed for each of the detectors in array 14.

Then the values of $\alpha_n$ and $\tau_n$ are employed to derive the constant terms of equation (5) for each of the four time constant components of every detector's response. These constants are stored in tables in the disc memory for later used in filtering real image data.

Another table in the memory is established to store a value of $S_{nk}$ for each detector in the array 14. At the beginning of a scan, the entries in this latter table are set to an initial value of zero. As each new filtered attenuation value is determined a new value for $S_{nk}$ is calculated and stored in the table.

Thereafter during normal operation of the CT system when attenuation values for real images are being acquired, the array processor of the computer processor 26 applies the filter function defined by equation (5) to the raw X-ray attenuation values. Depending upon the speed of the array processor the recursive filter function either can be applied in real-time as each detector sample is received from the data acquisition system 31 or the values can be stored temporarily in the memory and filtered later. Each raw X-ray attenuation value $y(k\Delta t)$ from the detector is used in equation (5) to filter out the effects due to the non-ideal response of the detector and calculate the actual, or filtered, value $x_k$ of the attenuation measurement. Separate constant terms and values for $S_{nk}$ are used for the samples from each detector. $S_{nk}$ is set to zero for the first sample from each detector during a given scan of the patient. Thereafter a new value for $S_{nk}$ is calculated for each detector every time another filtered attenuation value $x_k$ is derived.

Each filtered attenuation value is stored in another array in the disc memory 27. Conventional techniques are employed to reconstruct an image from the filtered data. The newly formed image is displayed on a monitor in the viewing console 29 and archived in magnetic tape unit 24.

The present filtering technique compensates not only for the effects of the primary speed component of the detector response, but also for the afterglow components. Although much of the non-ideal detector response is due to the primary speed, further improvement in the reconstructed image is achieved by considering the other time constant components of the detector response in the filter function.

I claim:

1. A medical imaging system comprising:
   a source of radiation;
   a detector for sensing radiation from said source and producing an output signal representing the sensed radiation, said detector having an exponential impulse response that is characterized by a plurality of N components having different time constants;
   means for periodically sampling the output signal from said detector to acquire a set of radiation attenuation values;
   means for recursive filtering the set of attenuation values to remove effects due to the exponential impulse response to produce a set of filtered values, said filtering means employs a filter function having terms for the plurality of impulse response components; and
   means for reconstructing an image from the set of filtered values.

2. The medical imaging system as recited in claim 1 wherein said means for recursive filtering produces a given filtered value $x_k$ by applying the following expression to each attenuation value $y(k\Delta t)$:

$$x_k = \frac{y(k\Delta t) - \sum_{n=1}^{N} (\beta_n e^{-\Delta t/\tau_n}) S_{nk}}{\sum_{n=1}^{N} \beta_n}$$

where k designates the value in the sets, $\Delta t$ is the periodic sampling interval, $\beta_n = \alpha_n (1 - e^{-\Delta t/\tau_n})$ in which $\alpha_n$ represents the strength of an impulse response component having time constant $\tau_n$, and $S_{nk} = x_{k-1} + e^{-\Delta t/\tau_n} S_{n(k-1)}$.

3. A method for operating a medical imaging system having a radiation detector with an impulse response which decays exponentially where the response is characterized by a plurality of components having different time constants, steps of the method comprising:
   exposing an object to be imaged to radiation;
   acquiring a set of attenuation values from the radiation detector;
   recursive filtering the set of attenuation values using a filter function, having terms which compensate for effects produced by each of the plurality of response components, to produce a set of filtered values; and
   reconstructing an image of the object from the set of filtered values.

4. The method for producing an image as recited in claim 3 which further comprises storing the attenuation values in a memory; and said recursive filtering step reads the attenuation values from the memory.

5. A method of operating a medical imaging system, steps of which comprising:
   exposing an object to a beam of radiation;
   acquiring a first set of radiation attenuation values by periodically sampling at an interval $\Delta t$ a signal produced by a radiation detector, where $y(k\Delta t)$ designates a value in the first set acquired during the kth sampling interval, the radiation detector having an impulse response that varies exponentially;
   producing a second set of data values from the first set of radiation attenuation values, in which each data value $x_k$ is defined by the equation:

$$x_k = \frac{y(k\Delta t) - \sum_{n=1}^{N} (\beta_n e^{-\Delta t/\tau_n}) S_{nk}}{\sum_{n=1}^{N} \beta_n}$$

where $\beta_n = \alpha_n(1 - e^{-\Delta t/\tau_n})$ in which $\alpha_n$ represents a relative strength Of an nth component of the impulse response which has time constant $\tau_n$, and $S_{nk} = x_{k-1} + e^{-\Delta t/\tau_n} S_{n(k-1)}$; and
   reconstructing an image of the object from the second set of data values.

6. The method as recited in claim 5 further comprising: characterizing the response of the detector to derive values of $\alpha_n$ and $\tau_n$ for each component used in producing the second set of data values.

7. The method as recited in claim 6 in which the step of characterizing the radiation response of the radiation detector comprises:

generating a beam of radiation which strikes the radiation detection from time $t_0$ to time $t_1$;

periodically sampling a signal produced by the radiation detector, such sampling occurs while the beam of radiation is being generated and continues until time $t_2$ which is later than time $t_1$, to produce a plurality of signal samples;

determining a time constant $\tau_n$ for each component of the impulse response;

calculating an X-ray flux intensity value $\Psi$ from a sample acquired between time $t_0$ and $t_1$; and deriving a value for $\alpha_n$ for each component of the impulse response from signal samples acquired between times $t_1$ and $t_2$ according to the expression:

$$y(t) = \Psi \sum_{n=1}^{N} \alpha_n e^{(t-t1)/\tau_n}.$$

8. The method as recited n claim 6 in which the step of characterizing the response of the detector comprises:

generating a beam of radiation from time $t_0$ to time $t_1$;

acquiring a first set of test radiation attenuation values by periodically sampling the signal produced by the radiation detector, such sampling occurs while the beam of radiation is being generated and continues until time $t_2$ which is later than time $t_1$;

determining a time constant $\tau_n$ for each component of the impulse response;

calculating an X-ray flux intensity value from a sample taken between times $t_0$ and $t_1$;

using the calculated X-ray flux intensity value to normalize signal samples acquired between times $t_1$ and $t_2$ and then taking the logarithm of the normalized signal samples;

deriving $\alpha_n$ for each component of the impulse response from said normalized signal samples, log-[y(T)], according to the expression log[y(T)]=log $\alpha_n - (T/\tau_n)$.

9. The method as recited in claim 8 in which the step of deriving $\alpha_n$ comprises:

(a) selecting a normalized signal sample that was acquired at a time T at which all the components of the impulse response can be neglected except the component which has the longest time constant $\tau_n$;

(b) solving the expression log[y(T)]=log $\alpha_n - (T/\tau_n)$ for $\alpha_n$;

(c) removing the effects of the component of the impulse response which has the longest time constant $\tau_n$ from the normalized signal samples;

(d) successively repeating steps (a) through (c) for each remaining components of the impulse response in descending order of time constant length, each time step (c) is executed the effects of the remaining component with the longest time constant $\tau_n$ are removed from the normalized signal samples.

* * * * *